(12) United States Patent
Schoen et al.

(10) Patent No.: US 9,221,049 B2
(45) Date of Patent: Dec. 29, 2015

(54) DEVICE AND METHOD FOR REMOVING A SUPERNATANT OF A LIQUID SAMPLE, AND USE OF A VALVE DEVICE HAVING A SOLUBLE MEMBRANE

(75) Inventors: Christian Schoen, Dresden (DE); Tanja Thiele, Herne (DE)

(73) Assignee: Boehringer Ingelheim Microparts GmbH, Dortmund (DE)

( * ) Notice: Subject to any disclaimer, the term of this patent is extended or adjusted under 35 U.S.C. 154(b) by 0 days.

(21) Appl. No.: 14/006,992

(22) PCT Filed: Mar. 23, 2012

(86) PCT No.: PCT/EP2012/055218
§ 371 (c)(1),
(2), (4) Date: Dec. 9, 2013

(87) PCT Pub. No.: WO2012/127034
PCT Pub. Date: Sep. 27, 2012

(65) Prior Publication Data
US 2014/0112841 A1    Apr. 24, 2014

(30) Foreign Application Priority Data
Mar. 24, 2011    (EP) .................................... 11002440

(51) Int. Cl.
*B01D 45/00*    (2006.01)
*B01L 3/00*    (2006.01)
(Continued)

(52) U.S. Cl.
CPC ................ *B01L 3/5021* (2013.01); *A61M 1/34* (2013.01); *B01D 63/00* (2013.01); *B01D 71/10* (2013.01); *B01D 2311/2676* (2013.01); *B01J 19/00* (2013.01); *B01L 3/14* (2013.01); *B01L 2300/0864* (2013.01);
(Continued)

(58) Field of Classification Search
CPC ........... B01D 2311/2676; B01D 63/00; B01D 71/10; B01L 3/14; B01L 3/5021; G01N 33/49; G01N 33/80; C12Q 1/22; A61M 1/34; B01J 19/00; E21B 25/08; E21B 25/00
USPC .................................... 422/44, 415, 506, 533
See application file for complete search history.

(56) References Cited

U.S. PATENT DOCUMENTS 3,897,337 A *  7/1975  Ayres ............................ 210/136
3,905,528 A     9/1975  Maiocco
(Continued)

FOREIGN PATENT DOCUMENTS

| DE | 1176402 B | 8/1964 |
| EP | 1935492 A1 | 6/2008 |
| WO | 2012127034 A1 | 9/2012 |

OTHER PUBLICATIONS

International Search Report and Written Opinion for PCT/EP2012/055218 mailed Aug. 24, 2013.

*Primary Examiner* — Dennis M White
(74) *Attorney, Agent, or Firm* — Michael P. Morris; Mary-Ellen M. Devlin

(57) ABSTRACT

A device and a method for separating a supernatant of a liquid sample are proposed, in which an outlet is closed off by a water-soluble membrane that dissolves after a certain length of time so that the supernatant of the sample is automatically drained away after centrifugation. The water-soluble membrane may in principle may also be used for other purposes for temporarily retaining a liquid in a holding chamber.

9 Claims, 1 Drawing Sheet

(51) Int. Cl.
  *E21B 25/00* (2006.01)
  *B01J 19/00* (2006.01)
  *G01N 33/80* (2006.01)
  *G01N 33/49* (2006.01)
  *B01D 71/10* (2006.01)
  *C12Q 1/22* (2006.01)
  *E21B 25/08* (2006.01)
  *B01D 63/00* (2006.01)
  *A61M 1/34* (2006.01)
  *B01L 3/14* (2006.01)

(52) U.S. Cl.
  CPC .......... *B01L 2400/0677* (2013.01); *C12Q 1/22* (2013.01); *E21B 25/00* (2013.01); *E21B 25/08* (2013.01); *G01N 33/49* (2013.01); *G01N 33/80* (2013.01)

(56) References Cited

U.S. PATENT DOCUMENTS

| | | | |
|---|---|---|---|
| 4,012,325 | A | 3/1977 | Columbus |
| 4,358,425 | A | 11/1982 | Finney et al. |
| 5,256,314 | A | 10/1993 | Driessen |
| 6,946,100 | B2 * | 9/2005 | Yokoi et al. .......... 422/415 |
| 2014/0112841 | A1 | 4/2014 | Schoen |

* cited by examiner

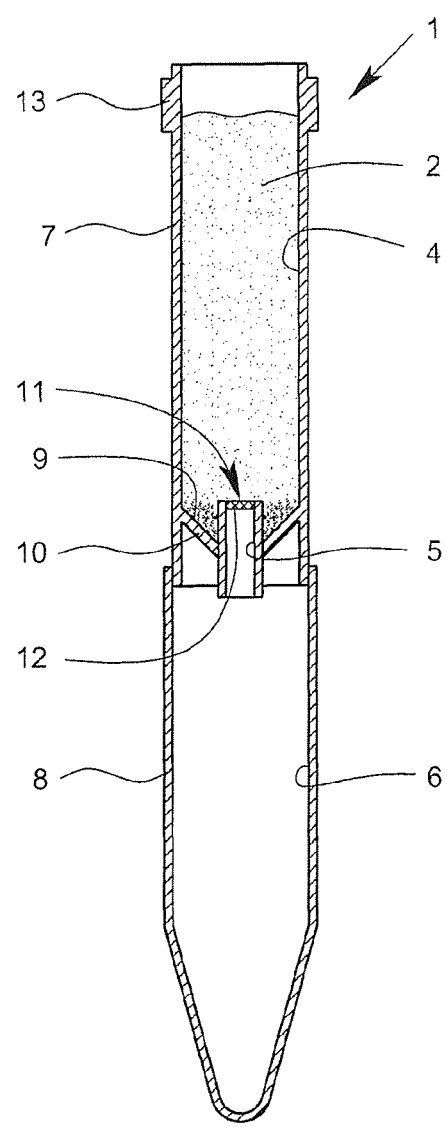

DEVICE AND METHOD FOR REMOVING A SUPERNATANT OF A LIQUID SAMPLE, AND USE OF A VALVE DEVICE HAVING A SOLUBLE MEMBRANE

The present invention relates to a device for removing a supernatant of a liquid sample according to the preamble of claim 1, a method for removing a supernatant of a liquid sample according to the preamble of claim 9 and a use of a valve device having a soluble membrane.

The present invention relates to the manipulation or concentration of a liquid sample, particularly a suspension. This is, in particular, a biological sample or sample liquid, particularly blood, urine or some other human or animal body fluid.

In order to concentrate solid constituents of a liquid sample, centrifugation may be carried out. However, a disadvantage up till now has been that the supernatant of the centrifuged sample has to be separated off or removed manually, for example using a pipette.

The present invention is based on the problem of providing a device and a method for removing a supernatant of a liquid sample and a use of a valve device having a soluble membrane, thus enabling or assisting with a simplified, particularly automated or automatic manipulation of the liquid sample.

The above problem is solved by a device according to claim 1, a method according to claim 9 or a use according to claim 15. Advantageous further features are the subject-matter of the sub-claims.

According to one aspect of the present invention, in order to remove a supernatant of a liquid sample, a holding chamber is provided with an outlet, the outlet having an associated valve device. Thus, the draining or removal of the supernatant from the liquid sample can be carried out deliberately or in controlled manner. In particular, first of all the sample may be centrifuged and then by opening the valve device the supernatant may be drained from the holding chamber and thus removed. This allows the liquid sample to be manipulated very easily. In particular, it is not necessary to use a pipette or the like for removing the supernatant.

The valve device preferably opens automatically and/or as a result of the dissolving of a membrane and/or by bursting when a particular pressure is reached or exceeded. This makes handling considerably easier.

According to another aspect of the present invention, the sample is centrifuged in the holding chamber and then drained off from the holding chamber—particularly by centrifugal and/or gravitational force—through an outlet that is temporarily closed and/or that opens automatically. This enables the structure to be very simple and promotes easy handling of the liquid sample.

Another aspect of the present invention lies in using a valve device having a soluble membrane for temporarily retaining a liquid in a holding chamber or for a normally closed valve device. The valve device opens automatically as a result of the membrane being partially or completely dissolved by the liquid. This enables the structure to be very simple and promotes easy handling of the liquid sample.

The present invention is particularly concerned with the concentration of solid constituents in the liquid sample. The concentrated constituents can then be subjected to further examination while the supernatant is separated or drained off and in particular can be discarded. However, in principle, the proposed valve device may also be used for other purposes.

The proposed solutions make it possible, in particular, to drain off or remove the supernatant without manual intervention and without interaction from the outside. Accordingly, the procedure and handling are made easier.

The above-mentioned aspects of the present invention and the aspects of the present invention explained hereinafter may be implemented in any desired combination but also independently of one another.

Further advantages, features, properties and aspects of the present invention will become apparent from the claims and the following description of a preferred embodiment by reference to the drawings. The single FIGURE shows:

A schematic section through a proposed device.

The FIGURE shows in schematic section a proposed device 1 for the manipulation of a liquid sample 2. In particular, the sample 2 is a particle-containing solution or suspension comprising, in particular, solid constituents 3. Particularly preferably, it is a biological sample or fluid, for example, blood, urine or some other human or natural body fluid. However, other fluids or suspensions or the like may also be handled as samples 2.

The device 1 is particularly preferably used for concentrating solid or insoluble constituents 3 of the sample 2 and/or for removing a supernatant of the sample 2, thus, in particular, the supernatant liquid after the concentration of the constituents 3.

The device 1 is used particularly for centrifugation. Particularly preferably, the device 1 can be inserted in a centrifuge (not shown) or be centrifuged.

In the embodiment shown the constituents 3 have already been concentrated in a lower region. The FIGURE thus shows, in particular, the state after centrifugation. The supernatant on the liquid or the sample 2, however, has not yet been removed or drained off.

The device 1 preferably comprises a holding chamber 4 for holding the sample 2 and an associated outlet 5 for draining off, particularly a supernatant of the liquid or sample 2. The device 1 may further comprise or form a collecting chamber 6 for the purpose of collecting the supernatant drained off through the outlet 5 or the liquid or the like drained off through the outlet 5.

In the embodiment shown, the holding chamber 4 is preferably formed in an upper part 7 of the device 1 and the collecting chamber 6 is preferably formed in a lower part 8 of the device 1. The upper part 7 and the lower part 8 are preferably embodied as separate components.

The lower part 7 and the upper part 8 are preferably releasably connectable to one another. The upper part 7 and the lower part 8 are preferably connected to one another by frictional or interlocking engagement, particularly by push-fitting, by screwing, by a bayonet closure, a snap-fit connection or the like. In particular, the lower part 8 can be pushed onto the upper part 7 or vice versa. In the representation shown in the single FIGURE the upper part 7 is connected to the lower part 8.

The upper part 7 and the lower part 8 may also be formed by a common component. The lower part 8 in this case may optionally be (completely) separable or releasable from the upper part 7 by means of a frangible point, for example. However, it is also possible for the upper part 7 and the lower part 8 not to be (completely) separable or releasable from one another.

In particular, the lower part 8 is held or secured to the upper part 7 such that the lower part 8 does not come away from the upper part 7 during the centrifuging of the sample 2 or device 1.

The device 1 is preferably configured to be at least substantially elongate or tubular and/or hollow-cylindrical. However, other configurations are also possible.

The outlet 5 is preferably arranged in an opposing end region or in a base region and/or in a region adjacent to the lower part 8.

The device 1 preferably comprises a retaining region 9 formed in the holding chamber 4 or upper part 7 and serving in particular to hold a residue of the sample 2, particularly the concentrated sample 2 or constituents 3, as schematically shown in the FIGURE. The retaining region 9 is preferably formed by an end wall portion or base 10 of the holding chamber 4 or upper part 7.

In the embodiment shown, the base 10 is preferably substantially funnel-shaped or conical.

In the embodiment shown the base 10 is preferably formed in one piece with the upper part 7. Preferably, the outlet 5 is formed in one piece with the upper part 7 or base 10.

The outlet 5 preferably extends into the holding chamber 4, particularly beyond the base 10 or retaining region 9 and into the holding chamber 4, so that when the outlet 5 is opened only liquid or supernatant above the retaining region 9 is drained out of the holding chamber 4 through the outlet 5. The outlet 5 thus opens into the holding chamber 4 above the base 10.

In the embodiment shown, the outlet 5 is preferably tubular or hollow-cylindrical in construction. In the embodiment shown the outlet 5 preferably extends in the main direction of extent of the device 1.

In the embodiment shown the holding chamber 4 or the upper part 7 is preferably embodied to be open at the top or at the end remote from the outlet 5 or base 10, in order to receive the sample 2.

It should be noted that the representation shows a preferred alignment of the device 1 in which the upper part 7 or holding chamber 4 is at the top, with the retaining region 9 at the bottom and the outlet 5 also arranged at the bottom. This alignment of the device 1 applies particularly when the liquid or supernatant drains or is supposed to drain through the outlet 5 by gravitational force. However, the device 1 may in principle have any other suitable alignment, particularly depending on the direction of any centrifugal force acting thereon, particularly preferably when the draining of the supernatant or liquid from the holding chamber 4 through the outlet 5 takes place or is supposed to take place by centrifugal force or (also) with the assistance thereof.

The upper part 7 or lower part 8 is preferably made of plastics and/or manufactured by injection moulding.

The device 1 preferably comprises a valve device 11 which is associated particularly with the outlet 5. The valve device 11 preferably closes off the outlet 5 temporarily or normally.

The valve device 11 is preferably configured so as to open automatically and/or after a predetermined time, particularly after the sample 2 has been transferred or received into the holding chamber 4.

The valve device 11 in the embodiment shown preferably comprises a membrane 12 or is formed thereby. The membrane 12 is preferably soluble, particularly in water. Particularly preferably, the membrane 12 is dissolved, partially dissolved or attacked by the sample 2. This opens the valve device 11 or membrane 12 or causes it to open or expose the outlet 5.

The time taken to open or expose the outlet 5 is preferably some minutes, particularly more than 10 minutes, particularly preferably more than 20 minutes. Thus, there is sufficient time left to centrifuge the device 1 or sample 2, for example, after the sample 2 has initially been transferred into the holding chamber 4. Then, the opening of the valve device 11 or membrane 12 takes place, as required, during or after centrifugation, for the purpose of removing the supernatant of the sample 2, i.e. the liquid above the opening of the outlet 5, or for draining it off from the holding chamber 4, particularly into the collecting chamber 6.

The membrane 12 is preferably of relatively thick-walled construction in order to withstand the stresses occurring during centrifugation.

Alternatively or additionally the valve device 11 or membrane 12 may also be embodied to open, break or burst on reaching or exceeding a specific pressure and/or a force acting thereon, particularly centrifugal force. Thus, for example, the valve device 11 or the membrane 12 and hence the outlet 5 can also be opened as a result of the centrifugal velocity or speed of rotation being increased so much, after a first centrifugation or after sufficient centrifuging, that the valve device 11 or the membrane 12 breaks or bursts or opens in some other way. The centrifugation may thus be carried out, for example, in two steps or at two velocities. Alternatively or additionally, the velocity or speed of rotation may also be increased continuously or gradually or in some other way.

The supernatant or the liquid located above the opening of the outlet 5 in the holding chamber 4 is preferably drained off from the holding chamber 4 through the outlet 5 by centrifugal and/or gravitational force after the opening of the valve device 11 or membrane 12.

The supernatant or liquid drained off is preferably caught or collected in the collecting chamber 6 of the lower part 8.

After the draining off of the supernatant the concentrated sample 2 remaining in the retaining region 9 can be further used, for example, for investigations or other operations. To assist with the removal of the concentrated sample 2 or concentrated constituents 3, the lower part 8 may be detached from the upper part 7 if required. Alternatively or additionally, the removal may also be carried out through the fill opening preferably located at the top of the holding chamber 4 or upper part 7; it may first be necessary to reopen this opening if it has been closed for the centrifugation, for example, by means for a stopper, seal or the like (not shown).

The volume of the retaining region 9 or of the sample 2 retained or concentrated in the collecting chamber 4 can be adjusted or fixed by the length of the drainage tube or the height of the opening of the outlet 5 in the holding chamber 4.

The valve device 11 or membrane 12 preferably closes off the outlet 5 in the manner of a stopper and/or over its entire surface and/or at least in fluidtight manner.

The valve device 11 or membrane 12 is preferably arranged at the holding chamber end or inlet end of the outlet 5, which is tubular in particular. However, the valve device 11 or membrane 12 may alternatively or additionally also be provided at the other end or outlet end of the outlet 5 and/or between the ends.

Alternatively, the outlet 5 may be at least substantially completely filled by the valve device 11 or by a material that is, in particular, water-soluble.

If required, a plurality of membranes 12 may also be used. Alternatively or additionally, a valve device 11 or membrane 12 may also be arranged at each end of the outlet 5.

The valve device 11 or membrane 12 preferably opens without any manual intervention from outside or other external action, particularly after a certain length of time or after a certain time has been exceeded, particularly preferably as a result of the liquid sample 2 or a constituent, particularly water, attacking, destroying, dissolving, partially dissolving and/or otherwise modifying the membrane 12 or some other part of the valve device 11.

The membrane 12 preferably contains a water soluble material. In particular, the membrane 12 is produced at least substantially or exclusively from a water-soluble material.

The valve device 11 or membrane 12 may be connected to the outlet 5 or inserted or introduced into it, for example, by adhesion, welding, clamping, press-fitting and/or by any other method.

The proposed valve device 11 or, in particular, water-soluble membrane 12 may in principle also be utilised or used for other valve purposes or for temporarily retaining a liquid 2, particularly in a holding chamber 4. The valve device 11 or membrane 12 then opens automatically, particularly as a result of at least partial dissolving of the material or membrane 12 by the liquid 2 or by a component of the liquid 2.

The device 1 or its upper part 7 preferably comprises at least one abutment 13, in the embodiment shown, particularly one or more lateral projections or the like for mounting in a centrifuge or the like (not shown).

LIST OF REFERENCE NUMERALS

1 Device
2 Sample
3 Constituent
4 Holding chamber
5 Outlet
6 Collecting chamber
7 Upper part
8 Lower part
9 Retaining region
10 Base
11 Valve device
12 Membrane
13 Abutment

The invention claimed is:

1. A device (1) for removing a supernatant of a liquid sample (2), comprising:
    a holding chamber (4) for the sample (2) having a proximal end and a distal end separated from one another along a longitudinal axis,
    a retaining region (9) disposed at the distal end of the holding chamber (4) and operating to collect constituents of the liquid sample that migrate towards the distal end of the holding chamber (4) during centrifugation,
    an outlet (5) having an entrance port and an exit port separated from one another along the longitudinal axis, the entrance port being located upstream from the retaining region (9) along the longitudinal axis such that the supernatant may flow into the entrance port while the constituents of the liquid sample remain within the retaining region (9), and
    a valve device (11) associated with the outlet (5) such that: (i) when the valve (11) is closed, the supernatant is blocked from flowing into the entrance port of the outlet (5); and (ii) when the valve (11) is open, the supernatant is permitted to flow into the entrance port of the outlet (5),
    wherein the retaining region (9), outlet (5) and valve (11) are fixed in position along the longitudinal axis within the holding chamber (4).

2. The device according to claim 1, wherein the entrance port of the outlet (5) is located upstream from the retaining region (9) along the longitudinal axis such that when the valve device (11) is open the supernatant of the sample (2) drains out of the holding chamber (4) only upstream of the retaining region (9).

3. The device according to claim 1, wherein the valve device (11) opens automatically.

4. The device according to claim 1, wherein the valve device (11) comprises a water-soluble membrane (12).

5. The device according to claim 1, wherein the valve device (11) opens or bursts when at least one of a predetermined pressure is exceeded, and after a predetermined time.

6. The device according to claim 1, wherein the device (1) comprises a collecting chamber (6) into which the exit of the outlet (5) communicates for the supernatant.

7. The device according to claim 6, wherein the device (1) comprises an upper part (7) and a lower part (8), the holding chamber (4) being arranged in the upper part (7) and the collecting chamber (6) being arranged in the lower part (8), and the upper part (7) and the lower part (8) are at least one of releasable from one another, and releasably connectable to one another.

8. The device according to claim 1, wherein the device (1) comprises at least one abutment (13) for mounting in a centrifuge.

9. The device according to claim 1, wherein the valve device (11) comprises a soluble membrane (12) for temporarily retaining the liquid (2) in the holding chamber (4), and the valve device (11) opens automatically as a result of the membrane (12) being at least partially dissolved by the liquid (2).

* * * * *